United States Patent
Pilgaonkar et al.

(10) Patent No.: US 10,286,024 B2
(45) Date of Patent: May 14, 2019

(54) **EXCIPIENT FROM *TRIGONELLA FOENUM-GRACEUM* SEEDS AND PROCESS FOR PREPARATION THEREOF**

(75) Inventors: Pratibha Sudhir Pilgaonkar, Maharashtra (IN); Maharukh Tehmasp Rustomjee, Maharashtra (IN); Anilkumar Surendrakumar Gandhi, Maharashtra (IN)

(73) Assignee: RUBICON RESEARCH PRIVATE LIMITED, Mumbai (IN)

( * ) Notice: Subject to any disclaimer, the term of this patent is extended or adjusted under 35 U.S.C. 154(b) by 0 days.

(21) Appl. No.: 13/639,890

(22) PCT Filed: Apr. 6, 2011

(86) PCT No.: PCT/IB2011/000744
§ 371 (c)(1),
(2), (4) Date: Oct. 8, 2012

(87) PCT Pub. No.: WO2011/124973
PCT Pub. Date: Oct. 13, 2011

(65) Prior Publication Data
US 2013/0041043 A1  Feb. 14, 2013

(30) Foreign Application Priority Data
Apr. 6, 2010  (IN) .................. 1152/MUM/2010

(51) Int. Cl.
| A61K 9/20 | (2006.01) |
| A61K 36/48 | (2006.01) |
| A61K 47/46 | (2006.01) |
| A23L 25/00 | (2016.01) |

(52) U.S. Cl.
CPC ............ *A61K 36/48* (2013.01); *A23L 25/30* (2016.08); *A61K 9/2068* (2013.01); *A61K 47/46* (2013.01)

(58) Field of Classification Search
None
See application file for complete search history.

(56) References Cited

U.S. PATENT DOCUMENTS

| 5,658,571 A | 8/1997 | Gopalan et al. |
| 5,847,109 A | 12/1998 | Garti et al. |
| 5,997,877 A | 12/1999 | Chang |
| 6,495,175 B2 | 12/2002 | Rao et al. |
| 2004/0228932 A1 | 11/2004 | Pilgaonkar et al. |
| 2005/0084549 A1* | 4/2005 | Pilgaonkar et al. .......... 424/757 |
| 2006/0269626 A1 | 11/2006 | Martinez et al. |
| 2008/0299235 A1 | 12/2008 | Aburdeineh et al. |

FOREIGN PATENT DOCUMENTS

| EP | 1697050 | 9/2006 |
| FR | 2 855 939 | 12/2004 |
| JP | 2002344842 | * 11/2002 |
| WO | 1996/040163 | 12/1996 |
| WO | 1999/025197 | 11/1998 |
| WO | 2001/074371 | 10/2001 |
| WO | 2005/009453 | 2/2005 |
| WO | 2005/049211 | 6/2005 |
| WO | 2009/057125 | 5/2009 |

OTHER PUBLICATIONS

Kay: Dietary Fiber; Journal of Lipid Research, vol. 23, 1982; pp. 221-242.*
Srichamroen et al. The Modifying Effects of Galactomannan From Canadian-Grown Fenugreek . . . on theGlycemic and Lipidemic Status in Rats; J. Clin. Biochem. Nutr., 43, 167-174 (No. 2008).*
Challem, J. Epidemic Proportions; Natural Foods merchandiser, Feb. 2009, pp. 32 and 34.*
Cicetti, F. Does Eating Oatmeal Lower Cholesterol?; Live Science, Online, URL<http://www.livescience.com/6234-eating-oatmeal-cholesterol.html> Mar. 2010 4 pages.*
Mathur et al. Fenugreek and Other Lesser Known Legume Galactomannan-Polysaccharides: Scope for Developments; Journal of Scientific & Industrial Research vol. 64, Jul. 2005, pp. 475-481.*
International Search Report for PCT/IB2011/000744 dated Jul. 25, 2011, 3 pgs.

* cited by examiner

*Primary Examiner* — Aaron J Kosar
(74) *Attorney, Agent, or Firm* — Blank Rome LLP

(57) ABSTRACT

An excipient from *Trigonella foenum-graceum* seeds and a process for preparation thereof is disclosed. The excipient obtained from *Trigonella foenum-graceum* seeds, comprising insoluble and soluble dietary fibers can be used in various pharmaceutical or cosmetic compositions and food, nutritional or dietary preparations.

18 Claims, No Drawings

US 10,286,024 B2

EXCIPIENT FROM *TRIGONELLA FOENUM-GRACEUM* SEEDS AND PROCESS FOR PREPARATION THEREOF

This application is a National Stage Application of PCT/IB2011/000744, filed 6 Apr. 2011, which claims benefit of Serial No. 1152/MUM/2010, filed 6 Apr. 2010 in India and which application(s) are incorporated herein by reference. To the extent appropriate, a claim of priority is made to each of the above disclosed applications.

FIELD OF THE INVENTION

The present invention relates to an excipient obtained from *Trigonella foenum-graceum* seeds and a process for preparation thereof. The invention further relates to an excipient obtained from *Trigonella foenum-graceum* seeds, comprising not less than 50% dietary fibers with ratio of insoluble dietary fibers to soluble dietary fibers of about 0.2 to about 1 and protein content of not more than about 10 weight %. The invention also relates to the use of this excipient in various pharmaceutical or cosmetic compositions and food, nutritional or dietary preparations.

BACKGROUND OF THE INVENTION

*Trigonella foenum-graceum* commonly known as fenugreek is an herbaceous plant of the leguminous family and is native to Western Asia, from where it has spread widely over Europe, the Mediterranean and rest of Asia. It is one of the oldest cultivated plants and through ages has found wide applications as a food, a food additive and as a traditional medicine in every region wherein it has been cultivated. The leaves and both the ripe and unripe seeds of *Trigonella foenum-graceum* are used as vegetables. The seeds also function as a food preservative and are added to pickles, chutneys and other similar food products. The ripe seeds have numerous applications in the traditional medicine system of India. Fenugreek has been used in treating colic flatulence, dysentery, diarrhea, dyspepsia with loss of appetite, chronic cough, dropsy, enlargement of liver and spleen, rickets, gout and diabetes.

The fenugreek seed contains a central hard yellow embryo surrounded by a corneous and comparatively large layer of white, semi-transparent endosperm. The endosperm is surrounded by a tenacious, dark brown testa. The endosperm and testa are referred to as husk. In mature seeds the majority of the endosperm cells are nonliving, the cytoplasmic content of which are occluded by the store reserves viz galactomannan. Fenugreek seed contains a large number of compounds such as volatile oil, fixed oils, proteins, carbohydrates, dietary fibers, hemicellulose, galactomannans, cellulose, saponins, resins, pigments, vitamins, minerals and others.

Typical analysis results of fenugreek seeds are documented in the table 1 hereunder:

TABLE 1

Typical analysis of fenugreek seeds

| | CONSTITUENT | PERCENTAGE |
|---|---|---|
| 1. | MOISTURE | 9.0 |
| 2. | ASH | 3.2 |
| 3. | LIPIDS | 7.0 |
| 4. | PROTEINS | 26.0 |
| 5. | STARCH | 1.6 |

TABLE 1-continued

Typical analysis of fenugreek seeds

| | CONSTITUENT | PERCENTAGE |
|---|---|---|
| 6. | FIBER | 48.0 |
| | Mucilage | 20.0 |
| | Hemicelluloses | 17.3 |
| | Cellulose | 8.2 |
| | Lignin | 2.5 |
| 7. | SAPONIN | 4.8 |
| 8. | TRIGONELLINE | 0.37 |

(Source: THE WEALTH OF INDIA, CSIR GOVT. OF INDIA PUBLICATION.)

Various seed components of *Trigonella foenum-graceum* along with the dietary fibers have an important role in the treatment and management of several disorders such as obesity, coronary heart disease, diabetes, piles, fissures, chronic constipation and diverticulitis. The saponins are reported to contain active components that are anti-carcinogenic, anti-microbial and/or anti-oxidant. The dietary fiber is the non-absorbable and indigestible fibrous portion, which is not assimilated by the body and is non-caloric and has substantially no nutrition value. It includes both soluble and insoluble fibers. Insoluble dietary fibers primarily comprise cellulose, lignin and some hemicelluloses; while soluble dietary fiber comprises pectin, gums and some hemicelluloses.

Owing to the versatile functionality of the various seed components of Fenugreek, attempts have been made to isolate these components using various processes. These processes mainly make use of organic solvents and/or specialized equipments for extraction of the components. Majority of these attempts emphasize upon isolation of fractions that include primarily soluble dietary fibers with high protein content.

U.S. Pat. No. 5,997,877 discloses a process for the fractionation of fenugreek seeds to provide various fractions thereof including a soluble dietary fiber fraction, de-flavored fenugreek seed, high protein fenugreek meal, dioscin and other saponins, along with fenugreek oleoresins. The process disclosed herein comprises tempering the fenugreek seed to moisture content in the range of 14% to 22%; flaking or milling the fenugreek seed; followed by solvent extraction and precipitation of the soluble gum. In one aspect the flaked fenugreek seeds are treated with polar alcohols at high temperatures to isolate oleoresin component prior to isolation of soluble dietary fiber; this process may however lead to loss of some amount of dietary fibers. Further, the soluble dietary fibers are isolated by heating the milled fenugreek over-fraction comprising endosperm and hull with water as a solvent at 60° C. for 4 hours which may affect the quality of the final product as well as the viscosity of the dietary fiber obtained. U.S. Pat. No. 6,495,175 discloses a method employing two different solvent extraction stages for obtaining substantially pure fixed oil, oleoresin and dietary fiber from Fenugreek seeds wherein the first extraction isolates fixed oils and the second extraction isolates oleoresin to finally provide dietary fibers that remain after extraction. Described herein is a special extraction system for better efficiency. Further the process disclosed in this application utilizes grinding and sieving of the fenugreek seeds for imparting higher surface area for better extraction which is well-known in the art. Use of high temperature, solvents and specialized extractor during the extraction process, makes the process very difficult on the commercial scale. Additionally, since the embryo is not separated from the dietary fiber at the time of grinding or isolation, the fibers obtained have higher protein content, which is not a desirable attribute for a pharmaceutical excipient.

U.S. Pat. No. 5,658,571 discloses a process for preparing debitterised powder of the fenugreek seed. Guar gum and bran are discussed to be blended with the debitterised powder of the seed of fenugreek to prepare formulations that can be used as fiber supplements. The process for debitterization of fenugreek seed disclosed involves the use of solvents and special jacketed extractor and therefore tends to have similar disadvantages as discussed above. The debitterised powder comprises a total dietary fiber of 48% by weight wherein the insoluble fiber is 28% by weight and the soluble fiber is 20% by weight. Further since the embryo is not separated from the dietary fiber during the preparation process, the debitterised powder is likely to have higher protein content, which is again not a desirable attribute for a pharmaceutical or food excipient. PCT Publication WO99/25197A1 discloses a fenugreek seed material having reduced odor and taste. The method of preparing the flaked/ground alcohol extracted fenugreek seed material, comprises the steps of: flaking a fenugreek seed to form a fenugreek preparation, extracting soluble components from the fenugreek preparation by extraction of the fenugreek preparation with an alcohol solvent at a cool extraction temperature to produce fenugreek solid; treating the fenugreek solid to remove the alcohol solvent to produce a dry solid; and grinding the dry solid into a powder to produce the fenugreek seed material. The process disclosed herein results in a product having a high amount of protein (about 20-40%), which not only reduces the amount of dietary fiber content in the end product but is also undesirable as a pharmaceutical and food excipient.

PCT Publication WO01/74371A1 discloses fenugreek mucilages and galactomannans. The fenugreek mucilages discussed herein are in the form of flour with grain size distribution less than 100 μm, consisting of 60 weight % of oses, relative to the composition total weight, namely mannose, galactose, glucose, arabinose, xylose, rhamnose, D-galacturonic acid with 50-55 weight % of doses consisting of galactomannans, and 5 weight % of proteins. The galactomannans disclosed further consist exclusively as doses, of mannose and galactose, with a mannose/galactose ratio of 1, 1.2. The key feature of the invention is pulverization of non-lipid fraction of fenugreek seed at sub-zero temperatures (−195 degrees) to improve the solubility of non-lipid fraction of fenugreek seed in the extracting solvent. This requires a specialized facility to carry out such an operation thereby increasing the cost of isolation of dietary fiber. U.S. Pat. No. 5,847,109 discloses an isolated galactomannan having at least 50 repeating units of mannose and galactose in a ratio of between 0.5-1.0 and 1.8-1.0, and having a protein content of less than 20 wt. %, a saponin content of less than 5 wt. %, and a lipid content of less than 1 wt. %. The process of isolation of galactomannan (soluble fiber) described herein involves use of organic solvents and high temperatures as well as specialized equipment. This process also involves treatment with polar alcohols that tend to reduce the yield of the soluble dietary fiber. The process further involves reduction in protein content by using chromatographic techniques that are difficult and expensive to carry out at commercial scale.

PCT Publication WO 2005/009453A1 discloses a process for the preparation of debitterised and defatted fenugreek powder containing 4-hydroxy isoleucine and rich in soluble dietary fiber. The process described includes extraction of powdered fenugreek seeds with ethanol/methanol to obtain debitterised powder containing 4-hydroxy isoleucine. This debitterised powder on sieving through a mesh size of 50 to 90 BSS yields upper and lower layers, of which upper layer is said to contain more of soluble fiber about 40 to 45%. That the fenugreek seeds are treated in this process with polar alcohols at elevated temperatures for debitterisation, the process may lead to loss of some amount of dietary fibers. Further since the entire seed with the husk and embryo is utilized in this extraction process, the debitterised powder obtained has higher protein content (20-45% by weight) which is an undesirable attribute for a pharmaceutical or food excipient. PCT Publication WO.2009/057125A1 discloses a process for improving the organoleptic property of the dietary fiber obtained from the seeds of fenugreek by debitterisation, deodourisation and decolourisation of the seed. The process disclosed herein consist of the steps of soaking the plant parts overnight in a solvent; powdering plant parts to obtain powder, extracting the powdered plant parts using a solvent; separating the extracted components, precipitating the separated components to obtain gum; and washing precipitated gum followed by drying to obtain organoleptically improved dietary fiber that comprises proteins around 25% and galactomannnans around 75%. Further since the entire seed is utilized in this extraction process, dietary fiber obtained has high protein content which is an undesirable attribute for a pharmaceutical or food excipient.

Thus methods disclosed in the art to isolate dietary fibers and other components from fenugreek seeds are non-specific and involve the use of costly and specialized equipments, organic solvents or energy intensive methods for extraction. Further the isolation of dietary fibers relates particularly to isolation of soluble dietary fibers for their therapeutic use or to isolation of soluble fibers with high protein content for nutritional purposes. Hence though attempts have been made towards isolating dietary fibers primarily soluble fibers, these have not been directed to isolation of dietary fibers from fenugreek having a particular ratio of insoluble to soluble fibers to obtain an excipient that can be used in various pharmaceutical or cosmetic compositions and food, nutritional or dietary preparations. Further various marketed products based on Fenugreek fibers available for health or nutritional purposes also mainly have soluble fibers in their compositions with insoluble dietary fibers if present being present at relatively low amounts. Fenfiber®, for example, manufactured by Emerald Seed Products for blood sugar and cholesterol management as well as for good digestive health, comprises 92% total fiber content with 80% soluble and 12% insoluble fibers i.e., has ratio of insoluble to soluble dietary fibers of 0.15. FenuPure from NatuR&D known to have properties of blocking the adsorption of glucose into blood and binding cholesterol implicated in heart disease has a total fiber content of greater than 85% and soluble fibers of greater than 80%, thereby having a ratio of insoluble to soluble fibers of about 0.07. Thus particularly the art fails to teach isolation of dietary fibers from fenugreek seeds comprising insoluble and soluble dietary fibers in a ratio of 0.2 to 1 and comprising not more than 10 weight % of protein.

EP1697050 discloses solvent free process of obtaining insoluble fiber rich fraction and further a highly purified fiber rich fraction from fenugreek seeds. The fractions obtained have at least 50% of dietary fiber with ratio of insoluble to soluble dietary fiber of greater than 0.8, preferably greater than 1.2 and a protein content of not more than 10 weight %. Though the solvent free process provides dietary fiber fractions with ratio of insoluble to soluble dietary fiber of greater than preferably 1.2, it does not disclose in any manner dietary fiber fractions or processes for obtaining the same wherein the ratio of insoluble to soluble fibers is lesser than 1 and protein content not more than 10 weight % that also exhibits necessary characteristics required of a pharmaceutical or food excipient such as viscosity, swelling index, water holding capacity etc.

Varying ratios of insoluble and soluble fibers and other constituents such as proteins in the extracts derived from fenugreek seeds determine the applicability of the extract as an excipient in pharmaceutical or cosmetic compositions and food, nutritional or dietary preparations. Excipients comprising insoluble and soluble fibers in a ratio of not more than 1 have properties and applications that are different from those comprising insoluble and soluble fibers in a ratio of more than 1. The differences in the chemical constitution and thereby the properties of soluble and insoluble dietary fibers results in differences in the applications of the products comprising them in varied ratios. Additionally in cases where the ratio of insoluble to soluble dietary fibers is less than 1, fiber based products with ratios of insoluble to soluble fibers of less than 0.2 do not possess properties desirable of pharmaceutical excipient. The present inventors after identifying the importance of varied ratio of insoluble to soluble fibers provide an excipient from fenugreek seeds comprising insoluble to soluble dietary fibers in a ratio of less than 1 with protein content of not more than 10 weight % and processes for production thereof. The excipient provided by the inventors of the present invention can be used industrially as a pharmaceutical or food excipient.

SUMMARY OF THE INVENTION

The present invention relates to an excipient obtained from *Trigonella foenum-graceum* seeds and a process for preparation thereof. The invention further relates to an excipient obtained from *Trigonella foenum-graceum* seeds, comprising not less than 50% dietary fibers with ratio of insoluble dietary fibers to soluble dietary fibers of about 0.2 to about 1 and protein content of not more than about 10 weight %. The invention also relates to the use of this excipient in various pharmaceutical or cosmetic compositions and food, nutritional or dietary preparations.

DETAILED DESCRIPTION OF THE INVENTION

The present invention provides an excipient obtained from *Trigonella foenum-graceum* comprising dietary fibers in an amount of not less than 50% dietary fibers by weight of the excipient, wherein said dietary fibers have a ratio of insoluble dietary fibers to soluble dietary fibers of about 0.2 to about 1; and protein content of not more than 10% by weight of the excipient. In one embodiment of the present invention an excipient obtained from *Trigonella foenum-graceum* is disclosed that comprises dietary fibers in an amount of not less than 50% by weight of the excipient, wherein said dietary fibers have a ratio of insoluble dietary fibers to soluble dietary fibers of about 0.2 to about 0.8; and protein content of not more than about 10% by weight of the excipient. In a further embodiment of the present invention an excipient obtained from *Trigonella foenum-graceum* is disclosed comprising dietary fibers in an amount of not less than 50% by weight of the excipient, wherein said dietary fibers have a ratio of insoluble dietary fibers to soluble dietary fibers of about 0.2 to about 0.7; and protein content of not more than about 10% by weight of the excipient. In a further embodiment of the present invention an excipient obtained from *Trigonella foenum-graceum* is disclosed comprising dietary fibers in an amount of not less than 50% by weight of the excipient, wherein said dietary fibers have a ratio of insoluble dietary fibers to soluble dietary fibers of about 0.3 to about 0.8; and protein content of not more than about 10% by weight of the excipient. In a further embodiment of the present invention an excipient obtained from *Trigonella foenum-graceum* is disclosed comprising dietary fibers in an amount of not less than 50% by weight of the excipient, wherein said dietary fibers have a ratio of insoluble dietary fibers to soluble dietary fibers of about 0.5 to about 0.8; and; protein content of not more than about 10% by weight of the excipient.

In yet another aspect of the present invention is provided an excipient comprising dietary fibers in an amount of about 50% to about 98% by weight of the excipient, wherein said dietary fibers have a ratio of insoluble to soluble dietary fiber of about 0.2 to about 1; and protein content of not more than 10 weight %. In another embodiment is provided an excipient comprising dietary fibers in an amount of about 50% to about 98% by weight the excipient, wherein said dietary fibers have a ratio of insoluble to soluble dietary fiber of about 0.2 to about 0.8 and; protein content of not more than 10 weight %. In one embodiment is provided an excipient comprising dietary fibers in an amount of about 50% to about 98% by weight the excipient, wherein said dietary fibers have a ratio of insoluble to soluble dietary fiber of about 0.2 to about 0.7 and; protein content of not more than 10 weight %. In a further embodiment is provided an excipient comprising dietary fibers in an amount of about 50% to about 98% by weight the excipient, wherein said dietary fibers have a ratio of insoluble to soluble dietary fiber of about 0.3 to about 0.8 and; protein content of not more than 10 weight %. In a still another embodiment of the present invention is provided an excipient obtained from *Trigonella foenum-graceum* comprising dietary fibers in an amount of not less than 50% by weight of the excipient, wherein said dietary fibers have a ratio of insoluble dietary fibers to soluble dietary fibers of about 0.2 to about 1 and protein content of not more than about 10 weight % having a viscosity greater than 10000 cps at 2% w/v concentration at 25° C. In another embodiment of the present invention is provided an excipient obtained from *Trigonella foenum-graceum* comprising not less than 50% dietary fibers with ratio of insoluble dietary fibers to soluble dietary fibers of about 0.2 to about 0.8 and protein content of not more than about 10 weight % having a viscosity greater than 10000 cps at 2% w/v concentration at 25° C. In a further embodiment of the present invention is provided an excipient obtained from *Trigonella foenum-graceum* comprising not less than 50% dietary fibers with ratio of insoluble dietary fibers to soluble dietary fibers of about 0.2 to about 0.7 and protein content of not more than about 10 weight % having a viscosity greater than 10000 cps at 2% w/v concentration at 25° C. In a one embodiment of the present invention is provided an excipient obtained from *Trigonella foenum-graceum* comprising not less than 50% dietary fibers with ratio of insoluble dietary fibers to soluble dietary fibers of about 0.3 to about 0.8 and protein content of not more than about 10 weight % having a viscosity greater than 10000 cps at 2% w/v concentration at 25° C. In a still another embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a swelling index greater than about 6 ml/g of excipient. In another embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a swelling index of about 6 ml/g of excipient to about 40 ml/g of excipient. In a still another embodiment of the present invention is provided an excipient obtained from *Trigonella foenum-graceum* comprising not less than 50% dietary fibers with ratio of insoluble dietary fibers to soluble dietary fibers of about 0.2 to about 0.8 and protein content of not more than about 10 weight % having a swelling index greater than about 6 ml/g of excipient. In a further embodiment of the present invention is provided an excipient obtained from *Trigonella foenum-graceum* comprising not less than 50% dietary fibers with ratio of insoluble dietary fibers to soluble dietary fibers of about 0.2 to about 0.7 and protein content of not more than about 10 weight % having a swelling index greater than about 6 ml/g of excipient. In another embodiment of the present invention is provided an excipient obtained from *Trigonella foenum-graceum* comprising not less than 50% dietary fibers with ratio of insoluble dietary fibers to soluble dietary fibers of about 0.3 to about 0.8 and protein content of not more than about 10 weight % having a swelling index greater than about 6 ml/g of excipient. In another embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a swelling index greater than about 15 ml/g of excipient. In one embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a swelling index of about 15 ml/g of excipient to about 40 ml/g of excipient. In one embodiment of the present invention is provided an excipient obtained from *Trigonella foenum-graceum* comprising not less than 50% dietary fibers with ratio of insoluble dietary fibers to soluble dietary fibers of about 0.2 to about 0.8 and protein content of not more than about 10 weight % having a swelling index greater than about 15 ml/g of excipient. In a further embodiment of the present invention is provided an excipient obtained from *Trigonella foenum-graceum* comprising not less than 50% dietary fibers with ratio of insoluble dietary fibers to soluble dietary fibers of about 0.2 to about 0.7 and protein content of not more than about 10 weight % having a swelling index greater than about 15 ml/g of excipient. In another embodiment of the present invention is provided an excipient obtained from *Trigonella foenum-graceum* comprising not less than 50% dietary fibers with ratio of insoluble dietary fibers to soluble dietary fibers of about 0.3 to about 0.8 and protein content of not more than about 10 weight % having a swelling index greater than about 15 ml/g of excipient. In a still another embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a water holding capacity greater than about 8 g of water/g of excipient. In another embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a water holding capacity of about 8 g of water/g of excipient to about 50 g of water/g of excipient. In one embodiment of the present invention is provided an excipient obtained from *Trigonella foenum-graceum* comprising not less than 50% dietary fibers with ratio of insoluble dietary fibers to soluble dietary fibers of about 0.2 to about 0.8 and protein content of not more than about 10 weight % having a water holding capacity greater than about 8 g of water/g of excipient. In another embodiment of the present invention is provided an excipient obtained from *Trigonella foenum-graceum* comprising not less than 50% dietary fibers with ratio of insoluble dietary fibers to soluble dietary fibers of about 0.2 to about 0.7 and protein content of not more than about 10 weight % having a water holding capacity greater than about 8 g of water/g of excipient. In a still another embodiment of the present invention is provided an excipient obtained from *Trigonella foenum-graceum* comprising not less than 50% dietary fibers with ratio of insoluble dietary fibers to soluble dietary fibers of about 0.3 to about 0.8 and protein content of not more than about 10 weight % having a water holding capacity greater than about 8 g of water/g of excipient. In another embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a water holding capacity greater than about 20 g of water/g of excipient. In one embodiment of the present invention is provided an excipient obtained from *Trigonella foenum-graceum* comprising not less than 50% dietary fibers with ratio of insoluble dietary fibers to soluble dietary fibers of about 0.2 to about 1 and protein content of not more than about 10 weight % having a water holding capacity of about 20 g of water/g of excipient to about 50 g of water/g of excipient. In one embodiment of the present invention is provided an excipient obtained from *Trigonella foenum-graceum* comprising not less than 50% dietary fibers with ratio of insoluble dietary fibers to soluble dietary fibers of about 0.2 to about 0.8 and protein content of not more than about 10 weight % having a water holding capacity greater than about 20 g of water/g of excipient. In another embodiment of the present invention is provided an excipient obtained from *Trigonella foenum-graceum* comprising not less than 50% dietary fibers with ratio of insoluble dietary fibers to soluble dietary fibers of about 0.2 to about 0.7 and protein content of not more than about 10 weight % having a water holding capacity greater than about 20 g of water/g of excipient. In still another embodiment of the present invention is provided an excipient obtained from *Trigonella foenum-graceum* comprising not less than 50% dietary fibers with ratio of insoluble dietary fibers to soluble dietary fibers of about 0.3 to about 0.8 and protein content of not more than about 10 weight % having a water holding capacity greater than about 20 g of water/g of excipient. In one aspect, viscosity, swelling index and water holding capacity are analyzed as per non-limiting illustrative examples discussed.

In a further embodiment of the present invention is provided an excipient comprising dietary fibers in an amount of not less than 50% dietary fibers by weight of the excipient, wherein said dietary fibers have a ratio of insoluble dietary fibers to soluble dietary fibers of about 0.2 to about 1; and protein content of not more than about 10% by weight of the excipient; wherein the excipient is further characterized by being substantially free of 4-hydroxyisoleucine. In one embodiment of the present invention is provided an excipient comprising dietary fibers in an amount of not less than 50% dietary fibers by weight of the excipient, wherein said dietary fibers have a ratio of insoluble dietary fibers to soluble dietary fibers of about 0.2 to about 0.8; and protein content of not more than about 10% by weight of the excipient; wherein the excipient is further characterized by being substantially free of 4-hydroxyisoleucine. In a further embodiment of the present invention is provided an excipient comprising dietary fibers in an amount of not less than 50% dietary fibers wherein said dietary fibers have a ratio of insoluble dietary fibers to soluble dietary fibers of about 0.2 to about 1; and protein content of not more than about 10% by weight of the excipient; wherein the excipient is further characterized by being substantially free of saponins. In one embodiment of the present invention is provided an excipient comprising dietary fibers in an amount of not less than 50% dietary fibers wherein said dietary fibers have a ratio of insoluble dietary fibers to soluble dietary fibers of about 0.2 to about 0.8; and protein content of not more than about 10% by weight of the excipient; wherein the excipient is further characterized by being substantially free of saponins. In a further embodiment of the present invention is provided an excipient comprising dietary fibers in an amount of not less than 50% dietary fibers wherein said dietary fibers have a ratio of insoluble dietary fibers to soluble dietary fibers of about 0.2 to about 1; and protein content of not more than about 10% by weight of the excipient; wherein the excipient is further characterized by being substantially free of alkaloids. In one embodiment of the present invention is provided an excipient comprising dietary fibers in an amount of not less than 50% dietary fibers wherein said dietary fibers have a ratio of insoluble dietary fibers to soluble dietary fibers of about 0.2 to about 0.8; and protein content of not more than about 10% by weight of the excipient; wherein the excipient is further characterized by being substantially free of alkaloids. In another embodiment of the present invention is provided an excipient comprising dietary fibers in an amount of not less than 50% dietary fibers wherein said dietary fibers have a ratio of insoluble dietary fibers to soluble dietary fibers of about 0.2 to about 1; and protein content of not more than about 10% by weight of the excipient; wherein the excipient is further characterized by being substantially free of 4-hydroxyisoleucine, alkaloids, saponins or sapogenins. In one embodiment of the present invention is provided an excipient comprising dietary fibers in an amount of not less than 50% dietary fibers wherein said dietary fibers have a ratio of insoluble dietary fibers to soluble dietary fibers of about 0.2 to about 0.8; and protein content of not more than about 10% by weight of the excipient; wherein the excipient is further characterized by being substantially free of 4-hydroxyisoleucine, alkaloids, saponins or sapogenins. In another embodiment of the present invention is provided an excipient comprising dietary fibers in an amount of not less than 50% dietary fibers wherein said dietary fibers have a ratio of insoluble dietary fibers to soluble dietary fibers of about 0.2 to about 1; and protein content of not more than about 10% by weight of the excipient; wherein the excipient is further characterized by being substantially free of 4-hydroxyisoleucine, alkaloids, saponins and sapogenins. In another embodiment of the present invention is provided an excipient comprising dietary fibers in an amount of not less than 50% dietary fibers wherein said dietary fibers have a ratio of insoluble dietary fibers to soluble dietary fibers of about 0.2 to about 0.8; and protein content of not more than about 10% by weight of the excipient; wherein the excipient is further characterized by being substantially free of 4-hydroxyisoleucine, alkaloids, saponins and sapogenins.

In one embodiment, the term "substantially free" as used herein means the excipient of the present invention obtained from *Trigonella foenum-graceum* may comprise not more than 1% by weight of 4-hydroxyisoleucine. In another embodiment, the term "substantially free" as used herein means the excipient of the present invention obtained from *Trigonella foenum-graceum* may comprise not more than 0.4% of 4-hydroxyisoleucine. In one embodiment, the term "substantially free" as used herein means the excipient of the present invention obtained from *Trigonella foenum-graceum* may comprise not more than 0.2% of 4-hydroxyisoleucine. In another embodiment, the term "substantially free" as used herein means the excipient of the present invention obtained from *Trigonella foenum-graceum* may comprise not more than 5% of alkaloids such as, but not limited to, trigonelline, gentianine, carpaine or choline and the like. In a further embodiment, the term "substantially free" as used herein means the excipient of the present invention obtained from *Trigonella foenum-graceum* may comprise not more than 1% of alkaloids such as, but not limited to, trigonelline, gentianine, carpaine or choline and the like. In another embodiment, the term "substantially free" as used herein means the excipient of the present invention obtained from *Trigonella foenum-graceum* may comprise not more than 0.5% of alkaloids such as, but not limited to, trigonelline, gentianine, carpaine or choline and the like. In a further embodiment, the term "substantially free" as used herein means the excipient of the present invention obtained from *Trigonella foenum-graceum* may comprise not more than 0.1% of alkaloids such as, but not limited to, trigonelline, gentianine, carpaine or choline and the like. In a further embodiment, the term "substantially free" as used herein means the excipient of the present invention obtained from *Trigonella foenum-graceum* may comprise not more than 5% of saponins such as, but not limited to, trigonelloside C, trigofoenoside A, trigofoenoside B, trigofoenoside C, trigofoenoside D, trigofoenoside E, trigofoenoside F, trigofoenoside G, trigoneosides Ia, trigoneoside Ib, trigoneoside IIa, trigoneoside IIb, trigoneoside IIIa, trigoneoside IIIb, neogitogenin, trigoneoside IX, trigoneoside Xa, trigoneoside Xb, trigoneoside XIb, trigoneoside XIIa, trigoneoside XIIb, trigoneoside XIIIa, graecunin H, graecunin I, graecunin J, graecunin K, graecunin L, graecunin M, graecunin N, fenugrin B. In a further embodiment, the term "substantially free" as used herein means the excipient of the present invention obtained from *Trigonella foenum-graceum* may comprise not more than 1% of saponins such as, but not limited to, trigonelloside C, trigofoenoside A, trigofoenoside B, trigofoenoside C, trigofoenoside D, trigofoenoside E, trigofoenoside F, trigofoenoside G, trigoneosides 1a, trigoneoside 1b, trigoneoside IIa, trigoneoside IIb, trigoneoside IIIa, trigoneoside IIIb, neogitogenin, trigoneoside IX, trigoneoside Xa, trigoneoside Xb, trigoneoside XIb, trigoneoside XIIa, trigoneoside XIIb, trigoneoside XIIIa, graecunin H, graecunin I, graecunin J, graecunin K, graecunin L, graecunin M, graecunin N, fenugrin B. In a further embodiment, the term "substantially free" as used herein means the excipient of the present invention obtained from *Trigonella foenum-graceum* may comprise not more than 0.5% of saponins such as, but not limited to, trigonelloside C, trigofoenoside A, trigofoenoside B, trigofoenoside C, trigofoenoside D, trigofoenoside E, trigofoenoside F, trigofoenoside G, trigoneosides Ia, trigoneoside Ib, trigoneoside IIa, trigoneoside IIb, trigoneoside IIIa, trigoneoside Mb, neogitogenin, trigoneoside IX, trigoneoside Xa, trigoneoside Xb, trigoneoside XIb, trigoneoside XIIa, trigoneoside XIIb, trigoneoside XIIIa, graecunin H, graecunin I, graecunin J, graecunin K, graecunin L, graecunin M, graecunin N, fenugrin B. In a further embodiment, the term "substantially free" as used herein means the excipient of the present invention obtained from *Trigonella foenum-graceum* may comprise not more than 0.1% of saponins such as, but not limited to, trigonelloside C, trigofoenoside A, trigofoenoside B, trigofoenoside C, trigofoenoside D, trigofoenoside E, trigofoenoside F, trigofoenoside G, trigoneosides Ia, trigoneoside Ib, trigoneoside IIa, trigoneoside IIb, trigoneoside IIIa, trigoneoside IIIb, neogitogenin, trigoneoside IX, trigoneoside Xa, trigoneoside Xb, trigoneoside XIb, trigoneoside XIIa, trigoneoside XIIb, trigoneoside XIIIa, graecunin H, graecunin I, graecunin J, graecunin K, graecunin L, graecunin M, graecunin N, fenugrin B. In a further embodiment, the term "substantially free" as used herein means the excipient of the present invention obtained from *Trigonella foenum-graceum* may comprise not more than 5% of sapogenins such as, but not limited to, diosgenin, yamogenin, yuccagenin, lilagenin, tigogenin, neotigogenin, gitogenin, neogitogenin, smilagenin, sarsapogenin. In a further embodiment, the term "substantially free" as used herein means the excipient of the present invention obtained from *Trigonella foenum-graceum* may comprise not more than 1% of sapogenins such as, but not limited to, diosgenin, yamogenin, yuccagenin, lilagenin, tigogenin, neotigogenin, gitogenin, neogitogenin, smilagenin, sarsapogenin. In a further embodiment, the term "substantially free" as used herein means the excipient of the present invention obtained from *Trigonella foenum-graceum* may comprise not more than 0.5% of sapogenins such as, but not limited to, diosgenin, yamogenin, yuccagenin, lilagenin, tigogenin, neotigogenin, gitogenin, neogitogenin, smilagenin, sarsapogenin. In a further embodiment, the term "substantially free" as used herein means the excipient of the present invention obtained from *Trigonella foenum-graceum* may comprise not more than 0.1% of sapogenins such as, but not limited to, diosgenin, yamogenin, yuccagenin, lilagenin, tigogenin, neotigogenin, gitogenin, neogitogenin, smilagenin, sarsapogenin.

In a further aspect the present invention provides process for obtaining an excipient, comprising not less than 50% dietary fibers with ratio of insoluble dietary fibers to soluble dietary fibers of about 0.2 to about 1 and protein content of not more than about 10 weight %. The process of the present invention utilizes equipments commonly employed in the pharmaceutical industry thereby simplifying scale-up and commercialization in comparison with prior art processes using specialized equipments.

The process steps involved in the preparation of excipient of the present invention from *Trigonella foenum-graceum* seeds have been discussed in further details beneath. Any modifications of the process steps apparent to a person skilled in the art are encompassed within the scope of the present invention.

(1) Selection of *Trigonella foenum-graecum* seeds of predetermined dimensions and swelling factor:

Seeds having length between 3.0-6.0 mm, preferably 3.5-4.5 mm and breadth ranging from 1.5-4.0 mm, preferably 2.0-3.5 mm are selected. Seeds with swelling factor ranging 0.5-50.0 ml, preferably 3.0-35.0 ml are used in the isolation process. Moisture content of the fenugreek seeds is also determined. Seeds with a moisture content of greater than 10% are difficult to process. In such cases the seeds are dried at 60° C. to achieve the moisture level of less than 10% and then subsequently employed for isolation of the excipient of the present invention.

(2) Roasting the selected seeds:

Seeds of *Trigonella foenum-graecum* are roasted to facilitate separation of embryo and husk. This step is carried out using a flaking drum or any other suitable equipment wherein seeds are roasted in a rotating drum at temperature >50° C. whereby the bond between the husk and embryo is loosened.

(3) Subjecting the seeds/roasted seeds to differential milling to obtain a mixture of embryo and husk The selected seeds roasted or non-roasted are milled to isolate the husk. The physical treatment process entails milling the selected roasted or non-roasted *Trigonella foenum-graceum* seeds in an impact three roller mill. Any mill such as, but not limited to comminuting mill, hammer mill, which is able to mill-break the *Trigonella foenum-graceum* seeds can be employed. Fenugreek seed is known to have central, hard yellow embryo, which is surrounded by husk comprising of corneous endosperm and tenacious testa. The differential milling operation results in physical separation of husk from the yellow embryo, to make a mixture of the two components physically together, but no longer physically attached to each other. In the differential milling process the embryo is milled due to its rigid nature and the husk being fibrous is not pulverized. In one embodiment the husk is further processed to separate the testa and the endosperm which can be blended in different proportions.

(4) Separation of husk from embryo

Separation of husk and the yellow embryo from the physical blend obtained after milling may be carried out by sieving through any sieve greater than 8#. The fraction passing through the sieve i.e., the yellow embryo-rich fraction is discarded and the fraction retained on the sieve is the fraction rich in husk. When employing roasted seeds, the husk fraction obtained after milling contains not more than 20% of embryo, preferably not more than 10% of embryo, more preferably not more than 5% of embryo. The husk fraction obtained after milling when non-roasted seeds are employed may still contain about 20% of the yellow embryo and further separation of this is carried out by a process based on the density difference between the husk and the yellow embryo. In another embodiment, the process of further separation of husk and embryo based on differential density between the two involves fluidization of the physical blend of fraction rich in husk and yellow embryo in a stream of air. As yellow embryo is denser than husk fraction, the husk is blown away during fluidization in a separate chamber whereas the yellow embryo remains in the same chamber. The husk-containing fraction is further sieved through 8# to obtain a husk rich excipient. The embryo content in husk-rich fraction is less than 20%, preferably less than 10%, preferably less than 5%.

(5) Sizing the separated husk to desired particle size:

The separated husk rich fraction is further milled using a roller mill, grinding mill or any other suitable mill to the desired particle size. This sized separated husk can be employed as excipient of the present invention that has unique properties resulting from the combination of soluble as well as insoluble dietary fiber.

(6) Tempering/hydrating the separated husk/separated sized husk/husk:

Tempering/hydrating the separated husk or separated sized husk or husk with demineralised water helps in sizing the fibrous husk to desired particle size distribution. Hydration is carried out using about 50% to about 200% demineralised water.

(7) Compaction and drying of the hydrated husk and sizing the compacted mass

Compaction of hydrated husk followed by drying and sizing also helps in sizing the fibrous husk to desired particle size distribution. Compaction of hydrated husk is carried out using flat rolls or any other suitable equipment known to a person skilled in the art. The compacted mass is dried using dryer to loss on drying of less than about 2%. Sizing of the compacted mass may be carried out by milling to obtain excipient of the present invention with desired particle size distribution and comprising not less than 50% dietary fibers with ratio of insoluble dietary fibers to soluble dietary fibers of about 0.2 to 1 and protein content of not more than 10 weight %.

(8) Purification of dietary fibers

The first step is preparation of dispersion of from about 0.1-10% w/v of sized husk/separated sized husk/separated husk/husk in a solvent. The process is carried out at room temperature and ambient atmospheric pressure; however, higher temperatures can be employed if necessary. Solvent used for extraction may be selected from water, acidified water or any other solvent in which the sized husk can produce dispersion. In one embodiment acetic acid is used for extraction as it results in increased yield and whiter product. The concentration of sized husk is only limited by the processibility as at higher concentrations due to increased viscosity stirring becomes difficult. The dispersion is then filtered or centrifuged. The insoluble fraction is subjected to further extraction using a solvent for better recovery.

The filtered dispersion is treated with an appropriate volume of a water-miscible, pharmaceutically acceptable solvent, which causes the precipitation of dietary fibers. Any of the pharmaceutically acceptable lower alkyl alcohols or ketones such as ethanol, methanol, isopropyl alcohol, acetone, and the like is suitable for precipitation and can be employed. In one embodiment methanol is used as a solvent. The ratio of the volumes of the water-miscible solvent to the dispersion may vary from about 1 to 5 to 5 to 1. To minimize the volume of solvent used, the volume of the dispersion may be reduced by evaporating water before adding the solvent. The resulting hairy fibers are separated from the liquids by any means known to one skilled in the art such as centrifugation or filtration.

(9) Washing the precipitate, followed by filtering, drying and sizing:

Further purification of the white hairy fibers is carried out using any of the pharmaceutically acceptable lower alkyl alcohols or ketones, such as, but not limited to, ethanol, isopropyl alcohol, acetone, and the like. This step removes the traces of moisture present in the fibrous precipitate and thereby aids in drying of the product at lower temperature conditions. The resulting excipient is dried at a temperature less than 100° C. for a period of time sufficient to dry the material to moisture content of less than 10%. Drying can be carried out using any of the equipments such as tray dryer, fluidized bed dryer, vacuum dryer etc. The conditions for drying are however very critical as high temperature, humidity and the rate of drying may cause discoloration of the product. Once the dried material is obtained it is further broken up to a suitable particle size by any means known in the art to obtain excipient of the present invention comprising not less than 50% dietary fibers with ratio of insoluble dietary fibers to soluble dietary fibers of about 0.2 to 1 and protein content of not more than 10 weight %.

(10) Spray-drying

Than washing the precipitated fibers, followed by filtering, drying and sizing, the separated purified dietary fibers of (8) above are alternatively resuspended and spray dried. Spray drying is an industrial process involving particle formation and drying. It is highly suited for the continuous production of dry solids in either powder, granulate or agglomerate form from liquid feedstock such as solutions, emulsions and pumpable suspensions. Spray drying involves the atomization of a liquid feedstock into a spray of droplets that are contacted with hot air in a drying chamber. The sprays are produced by rotary (wheel), nozzle, or ultrasonic atomizers. Evaporation of moisture from the droplets as the dry particles are formed proceeds under controlled temperature and airflow conditions. The dry product is discharged continuously from the drying chamber. Operating conditions and dryer design are selected according to the drying characteristics of the desired product, as is known in the art. There are a number of variables in the spray drying process, including feed composition, feed viscosity, density, feed spray rate, inlet temperature, outlet temperature, temperature difference, atomization pressure, vacuum and residence time, which can be varied in order to achieve the desired product. An illustrative process employed to produce the excipient of the present invention comprises dissolving/suspending the purified dietary fibers by homogenization in a suitable aqueous solvent, typically water or water miscible solvents to form slurry. The slurry may be preheated under stirring before being fed into the spray drying chamber, and may be sprayed with a single fluid nozzle or a two-fluid nozzle. Alternatively, the slurry may be sprayed using a rotating disk. The drying of the particles is achieved using any of the methods such as co-current flow, counter current flow or mixed flow. The total solid content of the feed could vary from about 0.05-75%.

Further some non-limiting embodiments describing the process employed to obtain excipient of the present invention comprising not less than 50% dietary fibers with ratio of insoluble dietary fibers to soluble dietary fibers of about 0.2 to about 1 and protein content of not more than about 10 weight % are discussed beneath.

In one embodiment a process for preparation of excipient of the present invention comprises a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain husk fraction containing not more than 20% of embryo, preferably not more than 10% of embryo, more preferably not more than 5% of embryo; e) sizing of the separated husk to obtain excipient of the present invention comprising not less than 50% dietary fibers with ratio of insoluble dietary fibers to soluble dietary fibers of about 0.2 to 1 and protein content of not more than 10 weight %.

Another embodiment relates to a process for preparation of excipient of the present invention comprising a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain husk fraction containing not more than 20% of embryo, preferably not more than 10% of embryo, more preferably not more than 5% of embryo; e) sizing of the separated husk; f) tempering/hydrating the sized husk with demineralised water; g) compacting and drying the mass; h) sizing the compacted mass to obtain excipient of the present invention comprising not less than 50% dietary fibers with ratio of insoluble dietary fibers to soluble dietary fibers of about 0.2 to 1 and protein content of not more than 10 weight %.

A still another embodiment relates to a process for preparation of excipient of the present invention comprising a) selecting *Trigonella foenum-graecum* seeds of predetermined dimensions and swelling factor; b) subjecting the seeds to differential milling to obtain a mixture of embryo and husk in which the embryo breaks in the form of particles; c) passing a mixture through a sieve to substantially separate the embryo and the husk, the separated husk fraction containing not more than 20% of embryo; d) separation of the husk from any embryo remnants based on density difference between them to provide separated husk containing preferably not more than 10% of embryo, more preferably not more than 5% of embryo; e) sizing of the separated husk; f) tempering/hydrating the sized husk with demineralised water; g) compacting and drying the mass; h) sizing the compacted mass to obtain excipient of the present invention comprising not less than 50% dietary fibers with ratio of insoluble dietary fibers to soluble dietary fibers of about 0.2 to 1 and protein content of not more than 10 weight %.

Another embodiment relates to a process for preparation of excipient of the present invention comprising a) selecting *Trigonella foenum-graecum* seeds of predetermined dimensions and swelling factor; b) subjecting the seeds to differential milling to obtain a mixture of embryo and husk in which the embryo breaks in the form of particles; c) passing a mixture through a sieve to substantially separate the embryo and the husk, the separated husk fraction containing not more than 20% of embryo; d) separation of the husk from any embryo remnants based on density difference between them to provide separated husk containing preferably not more than 10% of embryo, more preferably not more than 5% of embryo; e) sizing of the separated husk; f) analyzing the sized husk for its endosperm content or water holding capacity or swelling index or viscosity; g) selecting husk with an endosperm content of not less than 15% or a water holding capacity of not less than 6 g of water per g of husk or a swelling index of not less than 5 ml per g of husk or a viscosity of not less than 500 cps of 1% w/v solution; h) tempering/hydrating the selected sized husk with demineralised water; i) compacting and drying the mass; j) sizing the compacted mass to obtain excipient of present invention comprising not less than 50% dietary fibers with ratio of insoluble dietary fibers to soluble dietary fibers of about 0.2 to 1 and protein content of not more than 10 weight %.

Yet another embodiment relates to a process for preparation of excipient of the present invention comprising a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain husk fraction containing not more than 20% of embryo, preferably not more than 10% of embryo, more preferably not more than 5% of embryo; e) sizing of the separated husk; f) preparing a 2% w/v dispersion of sized husk in acidified water and sieving it to obtain translucent dispersion; g) precipitating fibers from translucent dispersion with polar alcohol; h) washing precipitate with solvents; i) filtering and drying; j) powdering to desired particle size to obtain excipient of the present invention comprising not less than 50% dietary fibers with ratio of insoluble dietary fibers to soluble dietary fibers of about 0.2 to 1 and protein content of not more than 10 weight %.

Another embodiment relates to a process for preparation of excipient of the present invention comprising a) selecting *Trigonella foenum-graecum* seeds of predetermined dimensions and swelling factor; b) subjecting the seeds to differential milling to obtain a mixture of embryo and husk in which the embryo breaks in the form of particles; c) passing a mixture through a sieve to substantially separate the embryo and the husk, the separated husk fraction contains some embryo portion; d) subjecting the separated husk again to milling and separation so as to obtain husk fraction containing not more than 20% of embryo; e) separation of the husk from any embryo remnants based on density difference between them to provide separated husk containing preferably not more than 10% of embryo, more preferably not more than 5% of embryo; f) sizing of the separated husk; g) preparing a 2% w/v dispersion of sized husk in acidified water and sieving it to obtain translucent dispersion; h) precipitating fibers from translucent dispersion with polar alcohol; i) washing precipitate with solvents; j) filtering and drying; k) powdering to desired particle size to obtain excipient of the present invention comprising not less than 50% dietary fibers with ratio of insoluble dietary fibers to soluble dietary fibers of about 0.2 to 1 and protein content of not more than 10 weight %.

Yet another embodiment relates to a process for preparation of excipient of the present invention comprising a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain husk fraction containing not more than 20% of embryo, preferably not more than 10% of embryo, more preferably not more than 5% of embryo; e) sizing of the separated husk; f) preparing a 2% w/v dispersion of sized husk in acidified water and sieving it to obtain translucent dispersion; g) precipitating fibers from translucent dispersion with polar alcohol; h) resuspending the precipitated fibers by homogenization followed by spray drying to obtain excipient of the present invention comprising not less than 50% dietary fibers with ratio of insoluble dietary fibers to soluble dietary fibers of about 0.2 to 1 and protein content of not more than 10 weight %.

Another embodiment relates to a process for preparation of excipient of the present invention comprising a) selecting *Trigonella foenum-graecum* seeds of predetermined dimensions and swelling factor; b) subjecting the seeds to differential milling to obtain a mixture of embryo and husk in which the embryo breaks in the form of particles; c) passing a mixture through a sieve to substantially separate the embryo and the husk, the separated husk fraction contains some embryo portion; d) subjecting the separated husk again to milling and separation so as to obtain husk fraction containing not more than 20% of embryo; e) separation of the husk from any embryo remnants based on density difference between them to provide separated husk containing preferably not more than 10% of embryo, more preferably not more than 5% of embryo; f) sizing of the separated husk; g) preparing a 2% w/v dispersion of sized husk in acidified water and sieving it to obtain translucent dispersion; h) precipitating fibers from translucent dispersion with polar alcohol; i) resuspending the precipitated fibers by homogenization followed by spray drying to obtain excipient of the present invention comprising not less than 50% dietary fibers with ratio of insoluble dietary fibers to soluble dietary fibers of about 0.2 to 1 and protein content of not more than 10 weight %.

In a further embodiment in order to prepare the excipient of the present invention with desired properties the separated husk or separated sized husk or husk may be selected with an endosperm content of not less than 15% or a water holding capacity of not less than 6 g of water per gram of material or a swelling index of not less than 5 ml per g of material or a viscosity of not less than 500 cps of 1% w/v solution. In another embodiment of the present invention the separated husk or separated sized husk or husk may be selected with an endosperm content of not less than 20% or a water holding capacity of not less than 6 g of water per gram of material or a swelling index of not less than 5 ml per g of material or a viscosity of not less than 500 cps of 1% w/v solution. In still another embodiment of the present invention the separated husk or separated sized husk or husk may be selected with an endosperm content of not less than 15% or a water holding capacity of not less than 6 g of water per gram of material or a swelling index of not less than 5 ml per g of material or a viscosity of not less than 2000 cps of 1% w/v solution. Selection of husk with the above parameters aids obtain excipient of the present invention with desired properties.

In one embodiment, the process for preparation of an excipient from *Trigonella foenum-graceum* seeds as per the present invention comprises: a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain separated husk fraction containing not more than 20% of embryo; and e) sizing of the separated husk.

In another embodiment, the process for preparation of an excipient from *Trigonella foenum-graceum* seeds as per the present invention comprises: a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain separated husk fraction containing not more than 20% of embryo; e) sizing of the separated husk; f) preparing a dispersion of sized separated husk in acidified water and sieving it to obtain translucent dispersion; g) precipitating fibers from translucent dispersion with polar alcohol; h) washing precipitate with solvents; i) filtering and drying; and j) powdering to desired particle size.

In one embodiment, the process for preparation of an excipient from *Trigonella foenum-graceum* seeds as per the present invention comprises: a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain separated husk fraction containing not more than 20% of embryo; and e) sizing of the separated husk; f) tempering/hydrating the sized separated husk with demineralised water; g) compacting and drying the mass; and h) sizing the compacted mass.

In one embodiment, the process for preparation of an excipient from *Trigonella foenum-graceum* seeds as per the present invention comprises: a) selecting *Trigonella foenum-graecum* seeds of predetermined dimensions and swelling factor; b) roasting the seeds to facilitate separation of embryo and husk; c) subjecting the roasted seeds to differential milling to obtain a mixture of embryo and husk in which the embryo breaks in the form of particles; d) passing a mixture through a sieve to substantially separate the embryo and the husk to obtain separated husk fraction containing not more than 20% of embryo; and e) sizing of the separated husk; f) tempering/hydrating the sized separated husk with demineralised water; g) compacting and drying the mass; h) sizing the compacted mass; i) preparing a dispersion of sized compacted mass in acidified water and sieving it to obtain translucent dispersion; j) precipitating fibers from translucent dispersion with polar alcohol; k) washing precipitate with solvents; l) filtering and drying; and m) powdering to desired particle size.

In one embodiment, the process for preparation of an excipient from *Trigonella foenum-graceum* seeds as per the present invention comprises: a) analyzing the *Trigonella foenum-graecum* seed husk or sized *Trigonella foenum-graecum* seed husk for its endosperm content or water holding capacity or swelling index or viscosity; and b) selecting husk with an endosperm content of not less than 15% or a water holding capacity of not less than 6 g of water per g of husk or a swelling index of not less than 5 ml per g of husk or a viscosity of not less than 500 cps of 1% w/v solution.

In another embodiment, the process for preparation of an excipient from *Trigonella foenum-graceum* seeds as per the present invention comprises: a) analyzing the *Trigonella foenum-graecum* seed husk or sized *Trigonella foenum-graecum* seed husk for its endosperm content or water holding capacity or swelling index or viscosity; b) selecting husk with an endosperm content of not less than 15% or a water holding capacity of not less than 6 g of water per g of husk or a swelling index of not less than 5 ml per g of husk or a viscosity of not less than 500 cps of 1% w/v solution; c) preparing a dispersion of selected husk or selected sized husk in acidified water and sieving it to obtain translucent dispersion; d) precipitating fibers from translucent dispersion with polar alcohol; e) washing precipitate with solvents; f) filtering and drying; and g) powdering to desired particle size.

In a still another embodiment, the process for preparation of an excipient from *Trigonella foenum-graceum* seeds as per the present invention comprises: a) analyzing the *Trigonella foenum-graecum* seed husk or sized *Trigonella foenum-graecum* seed husk for its endosperm content or water holding capacity or swelling index or viscosity; b) selecting husk with an endosperm content of not less than 15% or a water holding capacity of not less than 6 g of water per g of husk or a swelling index of not less than 5 ml per g of husk or a viscosity of not less than 500 cps of 1% w/v solution; c) tempering/hydrating the selected husk or selected sized husk with demineralised water; d) compacting and drying the mass; and e) sizing the compacted mass.

In a further another embodiment, the process for preparation of an excipient from *Trigonella foenum-graceum* seeds as per the present invention comprises: a) analyzing the *Trigonella foenum-graecum* seed husk or sized *Trigonella foenum-graecum* seed husk for its endosperm content or water holding capacity or swelling index or viscosity; b) selecting husk with an endosperm content of not less than 15% or a water holding capacity of not less than 6 g of water per g of husk or a swelling index of not less than 5 ml per g of husk or a viscosity of not less than 500 cps of 1% w/v solution; c) tempering/hydrating the selected husk or selected sized husk with demineralised water; d) compacting and drying the mass; e) sizing the compacted mass; f) preparing a 2% w/v dispersion of sized compacted mass in acidified water and sieving it to obtain translucent dispersion; g) precipitating fibers from translucent dispersion with polar alcohol; h) washing precipitate with solvents; i) filtering and drying; and j) powdering to desired particle size.

Another embodiment relates to a process for preparation of excipient of the present invention comprising a) selecting husk with an endosperm content of not less than 15% or a water holding capacity of not less than 6 g of water per g of husk or a swelling index of not less than 5 ml per g of husk or a viscosity of not less than 500 cps of 1% w/v solution; b) tempering/hydrating the selected husk with demineralised water; c) compacting and drying the mass; d) sizing the compacted mass to obtain excipient of the present invention comprising not less than 50% dietary fibers with ratio of insoluble dietary fibers to soluble dietary fibers of about 0.2 to 1 and protein content of not more than 10 weight %.

Another embodiment relates to a process for preparation of excipient of the present invention comprising a) selecting husk with an endosperm content of not less than 15% or a water holding capacity of not less than 6 g of water per g of husk or a swelling index of not less than 5 ml per g of husk or a viscosity of not less than 500 cps of 1% w/v solution; b) preparing a 2% w/v dispersion of selected husk in acidified water and sieving it to obtain translucent dispersion; c) precipitating fibers from translucent dispersion with polar alcohol; d) washing precipitate with solvents; e) filtering and drying; f) powdering to desired particle size to obtain excipient of the present invention comprising not less than 50% dietary fibers with ratio of insoluble dietary fibers to soluble dietary fibers of about 0.2 to 1 and protein content of not more than 10 weight %.

Still another embodiment relates to a process for preparation of excipient of the present invention wherein the husk can be employed in the form of separated endosperm and testa combined in various proportions ranging from but not limited to 1:99 to 99:1 to prepare the desired excipient.

In one embodiment the excipient of the present invention has the following characteristics.

| Parameter | Results |
| --- | --- |
| Dietary fibers | 50-85% |
| Insoluble dietary fibers (IDF) | 20-35% |
| Soluble dietary fibers (SDF) | 25-85% |
| IDF/SDF | >0.2 and <1 |
| Protein content | <10% |
| Viscosity at 2% w/v at 25° C. using Brookfield viscometer | >10,000 cps |
| Water holding capacity | >20 g of water/g of excipient |
| Swelling Index | >15 ml/g of excipient |

In another embodiment the excipient of the present invention has the following characteristics.

| Parameter | Results |
| --- | --- |
| Dietary fibers | 50-98% |
| Insoluble dietary fibers (IDF) | 15-40% |
| Soluble dietary fibers (SDF) | 55-85% |
| IDF/SDF | >0.2 and <1 |
| Protein content | <10% |
| Viscosity at 2% w/v at 25° C. using Brookfield viscometer | >50,000 cps |
| Water holding capacity | >20 g of water/g of excipient |
| Swelling Index | >15 ml/g of excipient |

In still another embodiment the excipient of the present invention is characterized as follows.

| Parameter | Results |
| --- | --- |
| Dietary fibers | 50-98% |
| Insoluble dietary fibers (IDF) | 15-35% |
| Soluble dietary fibers (SDF) | 25-75% |
| IDF/SDF | >0.2 and <1 |
| Protein content | <10% |
| Viscosity at 2% w/v at 25° C. using Brookfield viscometer | >10,000 cps |
| Water holding capacity | >8 g of water/g of excipient |
| Swelling Index | >6 ml/g of excipient |

In yet another embodiment the excipient of the present invention is characterized as shown beneath.

| Parameter | Results |
| --- | --- |
| Dietary fibers | 50-90% |
| Insoluble dietary fibers (IDF) | 10-35% |
| Soluble dietary fibers (SDF) | 55-85% |
| IDF/SDF | >0.2 and <1 |
| Protein content | <10% |
| Viscosity at 2% w/v at 25° C. using Brookfield viscometer | >10,000 cps |
| Water holding capacity | >8 g of water/g of excipient |
| Swelling Index | >6 ml/g of excipient |

The excipient of the present invention has unique properties in terms of dietary fiber content, ratio of insoluble to soluble dietary fiber, low protein content (despite of using minimum solvent and no lipophilic solvents like hexane and chloroform used) and desirable viscosity, water holding capacity or swelling index. Due to these features the excipient of this invention can be employed as an excipient in various pharmaceutical or cosmetic compositions and food, nutritional or dietary preparations. In one aspect the present invention relates to the use of the disclosed excipient in various pharmaceutical or cosmetic compositions and food, nutritional or dietary preparations. This excipient has a unique chemistry, having not only galactomannan but also celluloses, and hemicellulose, which contribute to the unique properties of the excipient. The excipient provided by the present invention is effective as a release-retarding polymer, disintegrant, binder, suspending agent, gelling agent, film forming agent, diluent and the like in pharmaceutical products and is also useful as a stabilizer, emulsifier, dispersant or rheology modifier in personal care, food, household care and industrial products. The excipient acts as a good release-retarding polymer for drugs with varying solubilities, particularly for highly soluble drugs, which are difficult to formulate in controlled release formulation. It also acts as a good suspending agent. It can be used in all liquid, semisolid and solid dosage forms. It can be formulated for oral, nasal, ocular, urethral, buccal, transmucosal, vaginal, topical or rectal delivery.

The word "excipient" as used herein implies pharmaceutically or physiologically inactive additive used in the manufacture of a pharmaceutical, cosmetic or nutritional composition or food or dietary preparations. In one embodiment the excipient of the present invention can be added to healthcare, personal care, food, household care or industrial products in an amount ranging from about 0.01% to about 95% by weight of the composition, depending on the purpose of use.

A pharmaceutical excipient allows the manufacture of a pharmaceutical formulation that provides for the necessary bioavailability of the medicament to the patient upon the administration of the composition. The bioavailability of a given dosage form is dependent on process variables and the interrelationship between the various excipients and the active ingredient. In one embodiment, the excipient of the present invention when used in solid dosage forms, can serve as, inter alia, a dry or wet binder that is used to hold together the structure of the dosage forms. In yet another embodiment, the excipient of the present invention can be used as disintegrant. The disintegration properties are based upon the ability of the excipient of the present invention to swell in the presence of a fluid such as water or gastric juice. This swelling disrupts the physical continuity of the structure of the dosage form, leading to its physical disintegration. In another embodiment, the excipient of the invention can be used as thickening agents in syrups, suspensions, emulsions or in syrups or suspensions for reconstitution. One of the important aspects of these dosage forms is the viscosity, which is required to prevent sedimentation rate of the solids in suspension and to achieve desired stability in case of emulsion and to arrive at a consistency suitable for administration in case of solutions. Thickening agent such as dietary fiber rich excipient imparts viscosity and is therefore an important additive in these formulations. The actual concentration of the excpient of the present invention can be selected based on the desired consistency. In still another embodiment, the excipient of the invention can be used as stabilizer for liquid dosage forms. It can be used as a suspending agent or as an emulsifying agent. It can also be employed as a thickening agent, base or gelling agent for these semisolid formulations. The concentration can be selected based on the desired consistency, appearance and the desired physical and chemical properties of the final product. In another embodiment, the excipient of the invention can be used as a coating agent for protecting the medicinal agent against destructive exposure to air and/or humidity, mask the taste of the drug, provide special characteristics of drug release and to provide aesthetic or distinction to the product. Commonly employed plasticizers such as polyethylene glycol, opacifiers or colorants can be used along with the excipient of the present invention for coating. In a further embodiment, the excipient of the invention can be used as release retarding polymer. The concentration of the excipient is based on the desired release profile, and the nature and dose of the active pharmaceutical ingredient. The excipient of the present invention can be used alone or in combination with the said polymers. The excipient of the present invention can be effectively used for drugs with varying solubilities and for controlled delivery of both lipophilic and hydrophilic drugs. Also, the excipient of the invention can be conveniently employed for large, medium and low dose drugs, alone or in combination. It can be incorporated in the various dosage forms that can be used for controlling the drug release such as capsules, tablets, micro granules, pellets, coated systems, etc. Further the excipient of the present invention can be employed for its polymeric and film forming property in the manufacturing of soft gelatin capsules. The excipient of the present invention can also act as an effective excipient in gastroretentive dosage forms. In yet another embodiment, the excipient of the invention can be used as structural component in films, devices or patches for transdermal applications. In a further embodiment the excipient can be incorporated in the following dosage forms: a capsule, a tablet, an ovule, a suppository, an insert, a wafer, a chewable tablet, a buccal tablet, a sublingual tablet, a quick-dissolve tablet, an effervescent tablet, a granule, a pellet, a bead, a pill, a sachet, a sprinkle, a film, an ointment, a cream, a gel, a dry syrup, a reconstitutable solid, a suspension, an emulsion, a lozenge, a troche, an implant, a powder, a triturate, a platelet, or a strip. These pharmaceutical compositions can be formulated for immediate release, pulsatile release; controlled release, extended release, modified release, delayed release, targeted release, or targeted delayed release. Also the compositions can be formulated for oral, nasal, ocular, urethral, buccal, transmucosal, vaginal, topical or rectal delivery. For development of these dosage forms this excipient can be combined with other excipients such as water soluble polymer, water insoluble polymers, hydrophobic materials, hydrophilic materials, waxes, disintegrants, superdisintegrants, diluents, binders, etc.

In a further embodiment the excipient of the present invention can be used in food, nutritional, dietary or personal care compositions as a stabilizer, emulsifier, dispersant or rheology modifier. It can also be used in household and industrial products as well. The excipient of the present invention can also be employed in cosmetic or personal care compositions to stabilize lotions and protective creams. It can also be used to increase the viscosity, assist in imparting spreading, add a smooth feel to the skin, and form a protective coating. The excipient of the present invention can also be used in personal care (such as, for example, hair and skin) products, to aid wetting of the skin, scalp or hair, facilitate dirt removal and dissolution, and ease rinsing after application. The excipient of the present invention can thus be used in personal care products as rheology modifiers, stabilizers, emulsifiers, binders, dispersants or film formers.

In the food industry, especially during the manufacture of ice creams, ice cream shakes and frozen desserts the excipient of the present invention can be used as stabilizer to maintain homogeneity, control ice crystal growth during the freezing or aeration process, and to provide slower and more uniform meltdown. The excipient of the present invention due to desirable water holding capacity is capable of binding quantities of water considerably larger than their weight and retarding the growth of ice crystals when the frozen food is subject to changes in temperature. Further, the excipient provides smooth texture and stability to dairy products and maintains their optimum quality for extended time periods. It can also help reduce syneresis in dairy products and prevent moisture migration. The excipient can be employed in baked foods to provide improved texture, mouth feel, softness, moisture-retention, shelf-life and fatty attributes to them. The excipient of the present invention can also be used to encapsulate flavors that are used in foods. In confectionaries the excipient of the present invention can be used as a stabilizer by retarding sugar crystallization or as emulsifiers and dispersants by emulsifying and distributing fat particles in the confectionary product. The excipient can also be utilized in the beverage industry to stabilize flavors and essential oils. The synergistic presence of fenugreek soluble dietary fiber and insoluble dietary fiber provides enhanced emulsification and stabilization properties and also serves as cloud-producing agent and foam-stabilizing agent in the beverage industry.

The excipient of the present invention can thus be used in food, fodder, pharmaceutical, personal care, household care and industrial products. It can be used in these products for various functions, without being limited only to the above mentioned list of applications.

While the present invention has been described in terms of its specific embodiments, certain modifications and equivalents will be apparent to those skilled in the art and are intended to be included within the scope of the present invention. The following examples merely illustrate the present invention and are not to be construed to limit, in any way, the scope of the invention.

EXAMPLES

1) Process for Preparation of Excipient of the Present Invention 5 kg Fenugreek seeds were purchased from a local source (Mumbai, India). Seeds were roasted using flaking drum wherein the seeds were roasted in a rotating drum at temperature of 80° C. Roasted seeds were introduced into the roller mill in a continuous process. The milled material was then collected and passed through a 16# sieve to substantially separate the embryo and the husk to obtain a husk fraction containing 3% of embryo. The amount of yellow embryo fraction in the separated husk was determined by physical separation of embryo remnants from the husk fraction. The separated husk (~3.5 kg) was hydrated by using about 50% demineralised water for about 90 minutes. Roll compaction of this hydrated husk was further carried out. The roll compacted mass was dried using fluidized bed dryer to loss on drying of less than about 2% and the compacted mass was then sized by milling to obtain 1 kg of excipient (I) of the present invention with not less than 65% having a particle size <250 μ.

2) Process for Preparation of Excipient of the Present Invention

Fenugreek husk samples obtained from local sources were analyzed for their viscosity. Husk with a viscosity of not less than 500 cps of 1% w/v solution was selected for the preparation of excipient. The selected husk (~5 kg) was hydrated by using about 50% demineralised water for about 90 minutes with mixing. Roll compaction of this hydrated husk was further carried out. The roll compacted mass was dried using fluidized bed dryer to loss on drying of less than about 2% and the compacted mass was then sized by milling to obtain 1.4 kg of excipient (II) of present invention with not less than 65% having a particle size <250 μ.

3) Process for Preparation of Excipient of the Present Invention 5 kg Fenugreek seeds were purchased from a local source (Mumbai, India). Seeds were roasted using flaking drum wherein the seeds were roasted in a rotating drum at temperature of 80° C. Roasted seeds were introduced into the roller mill in a continuous process. The milled material was then collected and passed through a 16# sieve to substantially separate the embryo and the husk to obtain a husk fraction. A dispersion of 250 g of the separated husk was prepared in acetic acid under stirring for 1 hr. The dispersion thus obtained was filtered through a 60# sieve to separate the dispersion from insoluble mass. The water insoluble fraction was again subjected to extraction for better recovery. All fractions were combined to give a volume of about 35 L. The dispersion thus obtained was treated with approximately half the quantity of methanol (~18 L), which resulted in the precipitation of dietary fibers. The white hairy mass thus obtained was filtered. Since the filtered white mass contains water bound to it, which may affect the properties of the final product and cause difficulty in drying the mass to obtain a powder, the moisture was removed by treating the fibers with acetone with neutralization step in between. Final washing of the product was given with acetone. The washed material thus obtained was dried at 60° C. for 9 hrs and powdered to obtain a 60# fraction of excipient (III) of the present invention.

4) Characterization of Excipient of the Present Invention

Characterization of excipient (3 samples) of the present invention prepared in examples 1, 2 and 3 above has been shown beneath in Table 1.

TABLE 1

| No. | Parameter | Excipient (I) of the present invention | Excipient (II) of the present invention | Excipient (III) of the present invention | Test Method |
|---|---|---|---|---|---|
| 1. | Dietary fibers (% w/w) | 90.09 | 90.21 | 94.20 | AOAC $18^{th}$ edition 2007, 985.29 |
|  | Insoluble dietary fibers (IDF) (% w/w) | 31.80 | 28.48 | 23.05 | AOAC $18^{th}$ edition 2007, 993.19 |
|  | Soluble dietary fibers (SDF) (% w/w) | 62.40 | 61.73 | 67.04 | AOAC $18^{th}$ edition 2007, 991.42 |
|  | IDF/SDF | 0.50 | 0.46 | 0.34 |  |
| 2. | Protein content (% w/w) | 5.5 | 3.9 | 4.9 | AOAC $18^{th}$ edition 2007, 984.13 |
| 3. | Viscosity (cps) | 1,00,000 | 1,10,000 | 1,60,000 | At 2% w/v at 25° C. using Brookfield viscometer |

TABLE 1-continued

| No. | Parameter | Excipient (I) of the present invention | Excipient (II) of the present invention | Excipient (III) of the present invention | Test Method |
|---|---|---|---|---|---|
| 4. | Water holding capacity (g of water/g of excipient) | 12 | 14 | 30.83 | Centrifugation and filtration method |
| 5. | Swelling Index (ml/g of excipient) | 8.33 | 9.5 | 22 | Ph. Eur 6.0 |

5) Comparative Evaluation of Viscosity, Water Holding Capacity and Swelling Index of Excipient of the Present Invention with Commercial Products (a) Comparative Data of Viscosities The viscosity of a 1% w/v solution of excipient (III of example 3) of the present invention, hydroxypropyl methylcellulose (Methocel K100M® and Methocel K4M® (obtained from Dow chemicals)), guar gum (Supercol K1), psyllium husk (Isaphagula) and Nutriose® (soluble fiber) was compared. 1% w/v solution of these polymers was prepared in distilled water and kept overnight for deaeration. Their viscosities were then determined at 25° C. using Brookfield viscometer LV model and are indicated below in Table 2.

TABLE 2

| No. | Polymers | Viscosity in cps |
|---|---|---|
| 1 | Methocel K100M | 2700 |
| 2 | Methocel K4M | 160 |
| 3 | Guar gum | 710 |
| 4 | Psyllium husk | 862.5 |
| 5 | Nutriose ® (soluble fiber) | 3 |
| 6 | Excipient of the present invention (III of example 3) | 10,000 |

This data suggests that the excipient of the present invention exhibited maximum viscosity compared to all other gums or polymers. This indicates that the excipient of the present invention can act as an effective controlled release excipient or a rheology modifier.

(b) Comparative Data of Swelling Index

The swelling index is the volume in milliliters occupied by 1 gram of test material after it has swollen in an aqueous liquid for 4 h. The swelling index of the excipient of the present invention was compared against that of guar gum (Supercol K1), psyllium husk (Isaphagula) and Nutriose® (soluble fiber) using the method laid down in European Pharmacopoeia 6.0. The method involved placing 1.0 g of the test material in a 25 ml ground-glass stoppered cylinder, which are shaken vigorously every 10 minutes for 1 hour and then allowed to stand for 3 hours. The volume occupied by the test material is measured, including any adhering mucilage. The results as depicted in the table 3 beneath clearly indicate that the swelling index of excipient is better than the other gums or fibers and comparable to psyllium husk.

TABLE 3

| Test material | Swelling Index (ml/g) |
|---|---|
| Excipient of the present invention (III of example 3) | 22 |

TABLE 3-continued

| Test material | Swelling Index (ml/g) |
|---|---|
| Guar gum (Supercol K1) | 15 |
| Psyllium husk (Isaphagula) | 25 |
| Nutriose ® (soluble fiber) | 0 |

This data indicates that the excipient of the present invention has high swelling index and can act as an effective excipient in gastroretentive dosage forms.

(c) Comparative Data of Water Holding Capacities

The water holding capacity of material is a measure of the ability of the material to immobilize water within its matrix. The centrifugation and filtration method was used to compare the water holding capacity of the excipient of the present invention against that of guar gum (Supercol K1), psyllium husk (Isaphagula) and Nutriose® (soluble fiber). For the centrifugation method tared centrifuge tubes each containing the specified amounts of material soaked for 24 h in distilled water were centrifuged at 10000 rpm for 20 min and the supernatant fraction was decanted. The fresh weight of material was determined and the water holding capacity was calculated as g water/g material. The results obtained as depicted beneath in table 4 clearly indicate that excipient of the present invention has a better water holding capacity than the other comparators.

TABLE 4

| Test material | Water Holding Capacity gm water/gm material |
|---|---|
| Excipient of the present invention (III of example 3) | 30.83 |
| Guar gum (Supercol K1) | 16 |
| Psyllium husk (Isaphagula) | 14 |
| Nutriose ® (soluble fiber) | 0 |

This data indicates that the excipient of the present invention can act as an effective ingredient in food and dietary preparations.

6) Use of Excipient of the Present Invention as a Controlled Release Agent

Excipient of the present invention can be used as a controlled release agent for a highly water soluble drug-propranolol hydrochloride as described in table 5 beneath.

TABLE 5

| Ingredients | Lot A (mg/unit) | Lot B (mg/unit) |
|---|---|---|
| Propranolol hydrochloride | 160 | 160 |
| Hydroxypropyl methyl cellulose, USP (Methocel ® K 100M) | 160 | — |
| Excipient III of example 3 | — | 160 |

TABLE 5-continued

| Ingredients | Lot A (mg/unit) | Lot B (mg/unit) |
|---|---|---|
| Magnesium stearate, USP | 1.6 | 1.6 |
| Colloidal silicon dioxide, USP | 3.4 | 3.4 |
| Total | 325 | 325 |

Propranolol hydrochloride in Lot A was blended with hydroxypropyl methyl cellulose and colloidal silicon dioxide and in Lot B was blended with the excipient of the present invention and colloidal silicon dioxide. The two lots were then compressed into tablets after lubrication with magnesium stearate. Dissolution was carried out in USP apparatus II (paddle) at 50 rpm using 900 ml dissolution media with 0.1N hydrochloric acid for 2 hours followed by dissolution testing in pH 6.8 phosphate buffer.

The dissolution profile is as indicated in the table 6 beneath.

TABLE 6

| Time intervals | Average % release | |
|---|---|---|
| (hrs) | Lot A | Lot B |
| 1 | 21.1 | 20.5 |
| 2 | 30.7 | 31.8 |
| 4 | 35.1 | 35.9 |
| 6 | 45.4 | 46.1 |
| 8 | 55 | 56.3 |
| 12 | 64.5 | 65 |
| 14 | 69.3 | 70.5 |

From the above data it can be concluded that the excipient of the present invention can be used as a controlled release agent for highly water-soluble drug such as propranolol hydrochloride. The release retarding properties of the excipient of the present invention are seen to be comparable to that of hydroxypropyl methyl cellulose.

7) Use of Excipient of the Present Invention as a Binder

Binding properties of the excipient of the present invention were compared against those of commercially used binders such as polyvinylpyrrolidone and copovidone. Tramadol hydrochloride was used as a model drug for this study. The drug was granulated using 1% binder solution with formulation A employing the excipient (III of example 3) of the present invention as a binder, formulation B employing polyvinylpyrrolidone as a binder and formulation C employing copovidone as a binder, the formed granules were then blended with the remaining ingredients and then lubricated and compressed.

TABLE 7

| | Formulations (mg/unit) | | |
|---|---|---|---|
| | A | B | C |
| Ingredients | | | |
| Tramadol hydrochloride | 100.00 | 100.00 | 100.00 |
| Microcrystalline cellulose, USP (Avicel PH101) | 186.00 | 186.00 | 186.00 |
| Croscarmellose sodium, USP/NF | 7.00 | 7.00 | 7.00 |
| Polyvinylpyrrolidone, USP/NF | — | 3.50 | — |
| Copovidone, USP | — | — | 3.50 |
| Excipient of the present invention (III of example 3) | 3.50 | — | — |
| Microcrystalline cellulose, USP (Avicel PH 102) | 44.50 | 44.50 | 44.50 |

TABLE 7-continued

| | Formulations (mg/unit) | | |
|---|---|---|---|
| | A | B | C |
| Croscarmellose sodium, USP/NF | 3.50 | 3.50 | 3.50 |
| Colloidal silicon dioxide, USP | 2.00 | 2.00 | 2.00 |
| Magnesium stearate, USP | 3.50 | 3.50 | 3.50 |
| Total | 350.00 | 350.00 | 350.00 |
| Physical parameters | | | |
| Hardness (N) | 45-50 | 40-50 | 40-50 |
| Friability (%) | NIL | NIL | NIL |
| Disintegration time (Sec) | 39-42 | 60-120 | 18-20 |

The above data shows that the physical parameters such as hardness, friability and disintegration time of the three formulations are comparable and therefore it can be concluded that the excipient of the present invention has good binding properties.

8) Evaluation of the Saponin Content of the Excipient of the Present Invention

The saponin content of the excipient of the present invention (III of example 3) was analyzed using HPLC method and the saponin content was found to be 0.92 weight %.

This data indicates that the excipient of the present invention has low saponin content as and therefore can be used as an excipient in pharmaceutical and cosmetic compositions.

The invention claimed is:

1. A pharmaceutical composition comprising:
   (i) a pharmaceutically active ingredient, and
   (ii) an excipient obtained from the husk fraction of *Trigonella foenum-graecum* seeds, wherein the excipient comprises (a) dietary fibers in an amount of not less than about 50% by weight of the excipient, said dietary fibers having a ratio of insoluble dietary fibers to soluble dietary fibers of about 0.2 to about 0.5, and (b) a protein content of not more than about 10% by weight of the excipient; wherein the excipient has a viscosity greater than 10,000 cps at 2% w/v concentration at 25° C., and wherein the entire excipient is obtained from the husk fraction of the *Trigonella foenum-graecum* seeds,
   wherein the composition is selected from ovules, suppositories, inserts, wafers, chewable tablets, buccal tablets, sublingual tablets, quick-dissolve tablets, effervescent tablets, granules, pellets, beads, pills, sachets, sprinkles, films, ointments, creams, gels, dry syrups, reconstitutable solids, suspensions, emulsions, lozenges, troches, implants, solutions, powders, triturates, and strips.

2. The composition according to claim 1, wherein the excipient has a swelling index of greater than about 6 ml/gram of excipient.

3. The composition according to claim 1, wherein the excipient has a water holding capacity of greater than about 8 grams of water per gram of excipient.

4. The composition according to claim 1, wherein the composition is formulated for immediate release, pulsatile release, controlled release, extended release, modified release, delayed release, targeted release, targeted delayed release, or any combination thereof.

5. The composition according to claim 1, wherein the composition is formulated for oral, nasal, ocular, urethral, buccal, transmucosal, vaginal, topical, or rectal delivery.

6. A pharmaceutical composition comprising:
(i) a pharmaceutical active ingredient, and
(ii) an excipient obtained from the husk fraction of *Trigonella foenum-graecum* seeds, wherein the excipient comprises (a) dietary fibers in an amount of not less than about 50% by weight of the excipient, said dietary fibers having a ratio of insoluble dietary fibers to soluble dietary fibers of about 0.2 to about 0.5, and (b) a protein content of not more than about 10% by weight of the excipient; wherein the excipient has a viscosity greater than 10,000 cps at 2% w/v concentration at 25° C., and wherein the entire excipient is obtained from the husk fraction of the *Trigonella foenum-graecum* seeds,
wherein the composition is a tablet or a capsule.

7. The composition according to claim 6, wherein the excipient has a swelling index of greater than about 6 ml/gram of excipient.

8. The composition according to claim 6, wherein the excipient has a water holding capacity of greater than about 8 grams of water per gram of excipient.

9. The composition according to claim 6, wherein the composition is formulated for immediate release, pulsatile release, controlled release, extended release, modified release, delayed release, targeted release, targeted delayed release, or any combination thereof.

10. The composition according to claim 6, wherein the composition is formulated for oral, nasal, ocular, urethral, buccal, transmucosal, vaginal, topical, or rectal delivery.

11. A pharmaceutical composition comprising:
(i) a pharmaceutical active ingredient, and
(ii) an excipient obtained from the husk fraction of *Trigonella foenum-gracum* seeds, wherein the excipient comprises (a) dietary fibers in an amount of not less than about 50% by weight of the excipient, said dietary fibers having a ratio of insoluble dietary fibers to soluble dietary fibers of about 0.2 to about 0.5, and (b) a protein content of not more than about 10% by weight of the excipient; wherein the excipient has a viscosity greater than 10,000 cps at 2% w/v concentration at 25° C., and wherein the entire excipient is obtained from the husk fraction of the *Trigonella foenum-graecum* seeds,
wherein the composition is a gastroretentive dosage form.

12. The composition according to claim 11, wherein the excipient has a swelling index of greater than about 6 ml/gram of excipient.

13. The composition according to claim 11, wherein the excipient has a water holding capacity of greater than about 8 grams of water per gram of excipient.

14. A composition comprising an excipient obtained from the husk fraction of *Trigonella foenum-graecum* seeds, wherein the excipient comprises (a) dietary fibers in an amount of not less than about 50% by weight of the excipient, said dietary fibers having a ratio of insoluble dietary fibers to soluble dietary fibers of about 0.2 to about 0.5, and (b) a protein content of not more than about 10% by weight of the excipient; wherein the excipient has a viscosity greater than 10,000 cps at 2% w/v concentration at 25° C., and wherein the entire excipient is obtained from the husk fraction of the *Trigonella foenum-graecum* seeds,
wherein the composition is selected from lotions, creams, tablets, capsules, granules, solutions, suspensions, beads, pellets, gels, emulsions, ovules, suppositories, inserts, wafers, chewable tablets, buccal tablets, sublingual tablets, quick-dissolve tablets, effervescent tablets, pills, sachets, sprinkles, films, ointments, creams, gels, dry syrups, reconstitutable solids, emulsions, lozenges, troches, implants, powders, triturates, strips, ice creams, ice cream shakes, frozen desserts, dairy products, confectionaries, baked foods, and beverages.

15. The composition according to claim 14, wherein the excipient has a swelling index of greater than about 6 ml/gram of excipient.

16. The composition according to claim 14, wherein the excipient has a water holding capacity of greater than about 8 grams of water per gram of excipient.

17. The composition according to claim 14, wherein the composition is formulated for oral, nasal, ocular, urethral, buccal, transmucosal, vaginal, topical, or rectal delivery.

18. A method of delivering a pharmaceutically active ingredient to a patient in need thereof comprising administering in an effective amount thereof a pharmaceutical composition comprising:
(i) a pharmaceutically active ingredient, and
(ii) an excipient obtained from the husk fraction of *Trigonella foenum-graecum* seeds, wherein the excipient comprises (a) dietary fibers in an amount of not less than about 50% by weight of the excipient, said dietary fibers have a ratio of insoluble dietary fibers to soluble dietary fibers of about 0.2 to about 0.5, and (b) a protein content of not more than about 10% by weight of the excipient; wherein the excipient has a viscosity greater than 10,000 cps at 2% w/v concentration at 25° C.,
wherein the composition is a tablet or a capsule.

* * * * *